Speaker et al.

[11] Patent Number: 4,917,892
[45] Date of Patent: Apr. 17, 1990

[54] ENCAPSULATED TOPICAL DELIVERY SYSTEM

[75] Inventors: Tully J. Speaker, Philadelphia; Frank N. Chang, Dresher; Stephen C. Hsu, Ambler, all of Pa.

[73] Assignee: Temple University, Philadelphia, Pa.

[21] Appl. No.: 212,492

[22] Filed: Jun. 28, 1988

[51] Int. Cl.$^4$ ................................................ A61K 6/00
[52] U.S. Cl. ...................................... 424/401; 424/78; 424/81; 424/423; 424/455; 424/486; 424/487
[58] Field of Search ............... 424/448, 449, 451, 455, 424/484, 423, 78, 426, 81, 486, 487, 425

[56] References Cited

U.S. PATENT DOCUMENTS

| | | | |
|---|---|---|---|
| 4,016,100 | 4/1977 | Suzuki et al. | 424/450 X |
| 4,145,408 | 3/1979 | Laughlin | 424/450 X |
| 4,485,054 | 11/1984 | Mezei et al. | 264/4.6 |
| 4,749,572 | 6/1988 | Ahari | 424/464 |
| 4,772,473 | 9/1988 | Vanlerberghe et al. | 424/59 X |

Primary Examiner—Thurman K. Page
Attorney, Agent, or Firm—Ratner & Prestia

[57] ABSTRACT

Delivery system for topical application comprising a highly viscous carrier containing dissolved or dispersed and microencapsulated topically-active agents providing immediate and sustained release of the topically-active agent to localized body sites.

20 Claims, No Drawings

ENCAPSULATED TOPICAL DELIVERY SYSTEM

BACKGROUND OF THE INVENTION

1. Field of the Invention

The invention relates to delivery systems for local application of topically-active agents to the body, especially for use in the treatment of local pathological or traumatic conditions which are difficult or impossible to treat with systemic medications. In particular, the invention relates to topical delivery systems containing high concentrations of pharmaceuticals or other topically-active agents for both immediate and sustained delivery to the affected body site.

2. Discussion of Related Art

Topical delivery systems for either the sustained or immediate release of topically-active agents are well-known. Of particular relevance are systems based on thermogel carriers, which are liquid at room temperature and gels at body temperature, and consequently promote retention at the treatment site of the pharmaceutical or other agent incorporated in the carrier. Delivery of naked pharmaceuticals (i.e., those merely dissolved or dispersed within the thermogel) is quite rapid, however, despite the occasional characterization of these systems as "sustained release", and these systems accordingly generally employ relatively low concentrations of pharmaceuticals as a therapeutic dosage to avoid excessive delivery.

Also of particular relevance to the invention are known "sustained release" preparations, typically comprising microencapsulated pharmaceuticals. While the pharmaceuticals are generally present in these systems in relatively high concentrations for gradual delivery over time, the systems are generally unsuitable in form for topical use.

The prior art has thus not provided topical delivery systems having a high concentration of topically-active agents which effectively deliver active agents to the treatment site both immediately and over an extended period of time.

Of particular interest herein is the treatment of the oral cavity for gingeval retractions, pits, pockets, and sulci; of the external auditory meatus; of the bony sinuses; of nasal passages and other mucosa-lined body orifices such as the vagina, rectum and urethra; and of punctures, abrasions, burns and other wounds. In the treatment of dental caries, fluoride-containing compositions, such as solutions or gels, are known for use in topical applications, since studies have shown that carie-resistance of tooth enamel increases when fluoride penetrates the enamel from a topical application. Therapeutic treatment of gingevitis often involves very elaborate and somewhat uncomfortable methods of treatment. For example, one known method involves implanting in the periodontal sulcus one or more coils of an antibiotic-impregnated cotton or nylon braided cord. The intent of this temporary implant is to provide a highly sustained localized topical drug delivery; the braided cord is used as a readily shaped device which can serve as a drug reservoir. Application of this implant can cause considerable discomfort to the patient and often multiple implantations are required. As a result, efforts have been directed to more convenient and less uncomfortable methods of treatment of gum disease such as the use of topical medicaments.

Topical medicaments for use in the oral cavity in the treatment of periodontal diseases which may be of relevance to the present invention are described in the following prior art:

Japanese Patent No. 61-418,125 pertains to the use of antibiotics in an ointment base for treating periodontal disease. An antibiotic is mixed with an anhydrous water-soluble ointment base which is applied in the gingival space, where it dissolves allowing rapid release of the antibiotic.

U.S. Pat. No. 4,454,110 is directed to a self-gelling composition for topical application of an active ingredient, for "sustained release" in the oral cavity. The gellable composition comprises a low viscosity, aqueous solution adapted to be converted after mixing and topical application from a liquid solution to a gel state.

U.S. Pat. No. 4,478,822 is directed to a drug delivery system consisting of a thermosetting gel in which an active ingredient is dispersed. This provides for a "prolonged time-release" of a drug from the gelled composition to the site of administration.

U.S. Pat. No. 4,329,333 and U.S. Pat. No. 4,597,959 pertain to a method and to a composition (respectively) in which a multiplicity of microencapsulated liquid droplets containing an active ingredient are applied to the gingival region and thus provide a "slow release" of the micro-encapsulated material into the oral cavity. The microcapsules containing the active ingredients are comprised of cross-linked gelatin materials which dissolve in the mouth and which are dispersed in a paste, cream, or gel.

BRIEF DESCRIPTION OF THE INVENTION

The present invention comprises a delivery system for topical application comprising a topically-active agent and a viscous carrier material, preferably a thermogel type gel-forming agent. The active agent is carried by the viscous carrier material both directly and indirectly within Lewis acid-Lewis base salt microparticulate materials dispersed within the viscous carrier material, and is consequently both immediately and gradually released to the treatment site. Methods of making these systems are also within the scope of this invention.

DETAILED DESCRIPTION OF THE INVENTION

The specific types of microparticulate material used in the present invention and methods for making such microparticulate material are disclosed in U.S. Pat. No. 3,989,457, (of partial common inventorship and common assignment herewith, and incorporated herein by reference). This material comprises the reaction product at the inter-phase boundary of a finely dispersed emulsion, comprising:

(I) a water-immiscible solution of an organic Lewis base or salt thereof in a low boiling point, slightly polar, organic solvent; and (II) an aqueous solution of a partially hydrophilic, partially lipophilic, polyfunctional Lewis acid or salt thereof.

Microparticles of this type comprise a multiplicity of closed structures formed of lattice-like high molecular weight salt molecules of the Lewis acid and Lewis base, through which an encapsulated therapeutic agent diffuses. The rate of diffusion is controlled by both the particle or molecular size of the encapsulated compound and by the openness of the lattice or network of molecules comprising the particle walls. The degree of openness of the lattice is controlled by the spacing of reactive sites on the high-molecular weight polyfunctional Lewis acids and the thickness of the particle walls.

Particularly suitable Lewis acids and bases and polar solvents for preparation of microparticulate material according to the process of U.S. Pat. No. 3,959,457 for use in the present invention are as follows:

Lewis acids: agar, acacia gum, arabic acid, carboxymethylcellulose, ghatti gum, guar gum, methylcellulose, oxidized cellulose, pectin, tragacanth, polyethylene glycol.

Polar solvents: bromoform, chloroform, dichloromethane, dichloroethane, diethyl ether, diisopropyl ether, methyl ethyl ketone, nitrobenzene.

Lewis bases: monofunctional amines, hexylamine, isopentylamine, n-methylpiperidine, piperidine, difunctional amines, dimethylethylenediamine, hexanediamine, piperazine, triethylenediamine, ethylenediamine, polyfunctional amines, hexamethylrosanilinium cation as chloride, rosanilinium cation as chloride, tetramethylrosanilinium cation as chloride, melamine, tetraethylpentamine, and triethyltetramine.

In addition to the free Lewis acids and based described in U.S. Pat. No. 3,959,457, salts of these acids and bases are readily employed as described herein to form the sustained release microcapsules of the present invention, and as more fully described in U.S. patent application Ser. No. 064,859, filed 19 Jun. 1987, and incorporated herein by reference. In this embodiment of the invention, salt pairs of Lewis acids and bases such as those exemplified in U.S. Pat. No. 3,959,457 are selected to react and form a neutral salt and a film-forming anisotropic salt in the reaction mixture in a double decomposition reaction. Useful salts are those which provide a pair of oppositely charged ions poorly soluble at the phase interface which are capable of reacting to form an anisotropic salt precipitate comprising the microcapsule wall. Preferably, the other pair of oppositely charged ions forms a neutral, fairly water-soluble salt. Exemplary Lewis acid and base salts suitable for this purpose include benzalkonium chloride, cetylpyridinium chloride, and alkali metal salts of carboxymethylcellulose, polyacrylic acid, or polyoxyethylene cross-linked with polyacrylic acid (e.g., Carbopol 934 TM, a product of B. F. Goodrich, Akron, OH).

Thermogel gelling agents useful in the delivery systems of the present invention comprise physiologically-compatible thermogels of the type known in the prior art. These gels are characterized by their property of changing from a fluid at or below room temperature to a gel at body temperature, and are thus well-adapted for localizing topically-active constituents for the duration of the treatment according to the invention. Suitable thermogels include polyoxy(ethylene/propylene) block copolymers (poloxamers) and their polyamine derivatives (poloxamines), as well as methylcellulose. Exemplary thermogels include those described in U.S. Pat. Nos. 4,478,822; 4,454,110; and 4,188,373; and Canadian Patent No. 1,072,413, especially the Pluronic TM and Tetronic TM polyols manufactured by Wyandotte Corp., Wyandotte, MI. In general, any physiologically-compatible gelling agent which forms an aqueous sol gel dispersion having the thermal gelation characteristics described above is useful in the practice of the present invention. The thermogel properties of the carrier allow the delivery system to be conveniently prepared and applied, while the carrier is in a fluid state, and to form a stable gel upon contact with the body, particularly the oral cavity.

The present invention thus provides a topically-applied delivery system for the immediate and sustained release of a pharmaceutical, cosmetic, or other topically-active agent to a localized body site, comprising a thermogel containing both dissolved and/or dispersed topically-active agent and microencapsulated topically-active agent.

Pharmaceuticals, cosmetics, or other active agents for topically treating the body suitable for use in conjuction with the thermogel carrier of the delivery system include antibacterial, antiviral, antiinflammatory, antifungal, antiprotozoal, ambecidal, and trichomonicidal pharmaceuticals, as well as anaesthetics, fluorides, analgesics and disinfecting agents, such as those described in U.S. Pat. No. 4,478,822. The microencapsulated agents for gradual release may be the same agents as the naked (unencapsulated) agents for immediate release, or may differ from the naked agents; the agents may also be variously mixed, as two or more naked agents combined with one or more microencapsulated agents.

In a particular embodiment of the invention, an antibiotic such as tetracycline is employed as the topically-active agent for topical application to the oral cavity to treat plaque-induced gingivitis at the tooth-gum interface to prevent periodontal destruction. The antibiotic is directly carried by the thermogel and indirectly by antibiotic-containing microcapsules dispersed within the thermogel, which is topically applied to the oral cavity. Other antibiotics may usefully be combined with tetracycline to treat gingivitis, depending on the causative microorganism. For example, as discussed in *Sci.* 239: 55–57 (1988), both *Bacteriodes gingivalis* and *Actinobacillus actinomycetemcomitans* have been implicated as microbiota associated with gingivitis. The use of one or more broad-spectrum or two or more narrow-spectrum antibiotics in combination against these microorganisms is contemplated.

GENERAL PROCEDURE FOR FORMING MICROENCAPSULATED TOPICALLY-ACTIVE AGENTS

In all instances where an aqueous solution is utilized as a continuous phase for the dispersion or emulsification of a second solution of materials dissolved in an organic solvent, it is preferred, but not essential, that the organic solvent be slowly and steadily added to the aqueous solution over a period of approximately thirty seconds. In all instances, solutions are prepared and reactions take place at room temperature, unless otherwise stated. Any of several means to disperse or emulsify the organic solution in the aqueous medium may be employed, including:

A. Vigorously stirring the solution with a magnetically driven stirring bar at a nominal sheer rate of 700 or more cm/s;

B. Vigorously mixing the solution with a multi-orifice axial turbine (such as a Brinkman Homogenizer PT 10/35 and generator PST/10 Brinkman Instruments, Westbury, N.Y.) at a nominal setting of 5; or C. Vigorously agitating the solution with an ultrasonic probe (such as Heat Systems Model W 185D, Ultrasonics, Inc., Plainview, N.Y.) at a nominal output of 100 watts.

By increasing or decreasing the length of time or vigor of the emulsification, droplet size (and resulting microparticle size) may be controlled. Typically, microparticle size ranges from 3 to 150 microns, although for specific applications larger or smaller particles may be desirable. Furthermore, it is preferred that sterile materials and aseptic techniques be employed in all steps.

The following Examples illustrate the practice of the invention:

EXAMPLE 1

As taught in U.S. Pat. No. 3,959,457, an aqueous solution of arabic acid was prepared by adding to one gram of arabic acid, enough water to make 10 mL. A non-aqueous solution was so prepared by adding anhydrous piperazine (in an amount stoichiometrically equivalent to the arabic acid), to enough dichloromethane to make 10 mLs of solution. Added to the dichloromethane solution was 250 mg of Tetracycline U.S.P. dissolved in 2.50 mL of diethyl succinate.

The aqueous and non-aqueous solutions were then combined in a container and continuously agitated for approximately one minute to produce a microencapsulated emulsion of organic droplets, approxiately 3 to 150 microns in diameter, dispersed in and surrounded by continuous aqueous phase solution.

After agitation, the emulsion was centrifuged at approximately 10,000 gravity minutes to separate the aqueous and non-aqueous phases as layers and to settle the newly-formed microcapsules to the bottom of the container. The aqueous phase was then removed along with any residual clear, non-aqueous liquid organic phase. Unreacted or excess reaction components were then removed by adding an equal amount of water to the microcapsules and subsequent removal of the added water. Residual dichloromethane was removed by evaporation, upon exposure of the aqueous suspension of the microcapsules to the atmosphere. Upon centrifugation and removal of supernatant water, the microparticulate material was rendered as a flowable concentrate of microcapsules. Upon drying, microparticulate material comprising microcapsules having shell-like films surrounding the core material, which included the tetracycline, was recovered.

The tetracycline-containing microcapsules were then suspended in 25 mL of an aqueous solution containing 500 mg of Ascorbic acid U.S.P. containing 250 mg of Tetracycline U.S.P.

In a separate container, 25 mL of 8% weight/volume suspension of Methylcellulose 4000 cps U.S.P. was prepared by adding the methylcellose to boiling distilled water. The methylcellulose suspension was stirred mechanically, while avoiding whipping additional air into the suspension. The suspension was then cooled to about 4 degrees Celsius whereupon the suspension of tetracycline-containing microcapsules in tetracycline solution was thoroughly mixed into the methylcellulose solution.

The resultant product comprised a thermogel solution containing dissolved and microencapsulated tetracycline antibiotics. This solution can readily be applied to the affected surface of a tissue region of a patient with a brush applicator, or by spraying, or instilled into sulci, pockets and depressions with the aid of a syringe or needle, or by other such methods which would be apparent to those skilled in the art.

EXAMPLE 2

As taught in U.S. Pat. No. 3,959,457, an aqueous solution of arabic acid was prepared by adding to one gram of arabic acid enough water to make 10 mL. A non-aqueous saturated solution/suspension was also prepared by adding to 4.0 mL of acetyldiethyl succinate 90 mg of tetracycline dihydrate, 10 mg of ascorbic acid and anhydrous piperazine (in an amount stoichiometrically equivalent to the combined arabic and ascorbic acids).

The aqueous and non-aqueous phases were combined in a container and continuously agitated for approximately one minute to produce an encapsulated emulsion of organic droplets, approximately 3 to 150 microns in diameter, dispersed in and surrounded by continuous aqueous phase.

After agitation, the encapsulated emulsion was centrifuged at approximately 20,000 gravity minutes to separate the aqueous and non-aqueous phases as layers and to settle the newly formed microcapsules to the bottom of the container. The aqueous phase was then removed along with any clear non-aqueous liquid phase. Unreacted or excess reaction components were then removed by addition of an equal volume of water to the microcapsules, resuspension, centrifugation and removal of the added water. Upon centrifugation and removal of the supernatant water, the microcapsular material was rendered as flowable concentrate.

Without further treatment the microcapsules were suspended in a chilled medium consisting of a solution of 10 mg of tetracycline dihydrate, 90 mg of ascorbic acid and 1800 mg of Methocel A15LV methylcellulose, a brand name product of Dow Chemical Co., Midland, MI in enough water to make 18 mL.

EXAMPLE 3

A flowable concentrate of microcapsules as described in Example 2 was made. Without further treatment the microcapsules were suspended in a chilled medium consisting of a solution of 10 mg of tetracycline dihydrate, 90 mg of ascorbic acid, 100 mg meglumine triazoate and 1700 mg of Methocel A15LV methylcellulose, a brand name product of Dow Chemical Co., Midland, MI in enough water to make 18 mL.

The formulation of Example 3 contains a radiopaque agent and so may be useful if there is uncertainty as to the extent to which an infected sulcus has been filled with medication. The radiopaque agent makes the volume filled by the medication containing it more readily distinguishable in x-ray films of the treated area from surrounding soft or bony tissue and from more highly radiolucent void spaces. Thus, the inclusion of a radiopaque agent in the formulation affords the practitioner a facile and unambiguous means by which to assess the accuracy and completeness of application of the medication.

The examples provided utilize both high and low viscosity forms of methylcellulose. The high viscosity form used in Example 1 produces a thermogel with a comparatively small gradient of viscosity with temperature. Thus, it is better suited to applications in which a relatively thick preparation offers the advantage of flowing less under the influence of gravity before it has completely warmed and gelled. The high viscosity formulation may be preferred by some practitioners in treatment of infected tissue which has a downward opening orifice as might be found in periodontal disease affecting teeth of the upper jaw. The low viscosity form of methylcellulose employed in Examples 2 and 3 exhibits a greater change in viscosity with change in temperature; it is more fluid when chilled to the same temperature than is the methylcellulose form used in Example 1. Accordingly, chilled formulations made with low viscosity methylcellulose are easier to apply to infected tissue having an upward opening sulcus such as might be found in periodontal disease of the lower jaw or in infections in which the path by which the medication is to be introduced is convoluted or tortuous as in the external auditory canal.

We claim:

1. A delivery system for the immediate and sustained topical application of at least one topically-active agent to a localized area of the body comprising a viscous carrier containing a dissolved or dispersed topically-active agent and a topically-active agent microencapsulated within a semipermeable anistropic salt film which is the emulsion reaction product of a) a partially lipophilic, partially hydrophilic, polyfunctional Lewis acid or salt thereof in aqueous medium with b) a Lewis base or salt thereof in a water-immiscible, slightly polar organic solvent for the base.

2. The delivery system of claim 1, wherein the viscous carrier is a thermogel.

3. The delivery system of claim 2, wherein the thermogel contains at least two different topically-active agents.

4. The delivery system of claim 1 wherein the localized area of the body is the oral cavity.

5. The delivery system of claim 4, wherein the localized area of the body is the periodontal region.

6. The delivery system of claim 1, wherein the topically-active agent is a pharmaceutical, cosmetic, or anaesthetic.

7. The delivery system of claim 5, wherein at least one of the topically-active agents is an antibiotic.

8. The delivery system of claim 2, wherein said Lewis acid or salt thereof is acacia gum, arabic acid, carboxymethylcellulose, methylcellulose, oxidized cellulose, pectin, tragacanth, ghatti gum, guar gum, polyethylene glycol, agar, sodium carboxymethylcellulose, or an alkali metal salt of polyacrylic acid or polyoxyethylene cross-linked with polyacrylic acid.

9. The delivery system of claim 8, wherein said Lewis base or salt thereof is hexylamine, isopentylamine, n-methylpiperidine, piperidine, dimethylenediamine, hexanediamine, piperazine, triethylenediamine, ethylenediamine, hexamethylrosanilium cation, rosanilium cation, tetramethylrosanilium cation, melamine, tetraethylpentamine, triethyltetramine, benzalkonium chloride, or cetylpyridinium chloride.

10. The delivery system of claim 2, wherein the thermogel is a poloxamer, poloxamine, or methylcellulose.

11. A method for preparing the delivery system of claim 1, comprising (a) mixing together (i) a partially hydrophilic, partially lipophilic, polyfunctional Lewis acid or salt thereof in an aqueous medium, (ii) a water-immiscible solution of a Lewis base or salt thereof in a slightly polar solvent for the Lewis base, and (iii) a first topically-active agent, with agitation to form an aqueous suspension of microcapsules encapsulating and semipermeable to the first topically-active agent;

(b) recovering a concentrate of the microcapsules from the aqueous suspension thereof;

(c) forming an aqueous thermogel solution; and (d) combining the microcapsule concentrate, the thermogel solution, and a second topically-active agent to form said delivery system.

12. The method of claim 11, wherein the first topically-active agent is first combined with the water-immiscible solution of Lewis base or salt thereof before admixing with the Lewis acid or salt thereof in aqueous medium.

13. The method of claim 11, wherein the microcapsule concentrate is resuspended in an aqueous solution or dispersion of the second topically-active agent before combining with the thermogel solution.

14. The method of claim 11, wherein the second topically-active agent is admixed with the thermogel solution before combining with the microcapsule concentrate.

15. The method of claim 11, wherein the first and second topically-active agents are different.

16. The method of claim 11 wherein the thermogel is a poloxamer, poloxamine, or methylcellulose.

17. The method of claim 11, wherein the Lewis acid or salt thereof is acacia gum, arabic acid, carboxymethylcellulose, methylcellulose, oxidized cellulose, pectin, tragacanth, ghatti gum, guar gum, polyethylene glycol, agar, sodium carboxymethylcellulose, or an alkali metal salt of polyacrylic acid or polyoxyethylene cross-linked with polyacrylic acid.

18. The method of claim 11, wherein the Lewis base or salt thereof is hexylamine, isopentylamine, n-methylpiperidine, piperidine, dimethylenediamine, hexanediamine, piperazine, triethylenediamine, ethylenediamine, hexamethylrosanilium cation, rosanilium cation, tetramethyrosanilium cation, melamine, tetraethylpentamine, triethyltetramine, benzalkonium chloride, or cetylpyridinium chloride.

19. The method of claim 11, wherein either the first or second topically-active agent, or both, is an antibiotic.

20. The method of claim 11, wherein the first and second topically-active agents are pharmaceuticals, cosmetics, or anaesthetics.

* * * * *